(12) United States Patent
Yao

(10) Patent No.: US 12,383,272 B2
(45) Date of Patent: Aug. 12, 2025

(54) COMPOSITE NEURAL CONDUIT

(71) Applicant: Wichita State University, Wichita, KS (US)

(72) Inventor: Li Yao, Wichita, KS (US)

(73) Assignee: Wichita State University, Wichita, KS (US)

( * ) Notice: Subject to any disclaimer, the term of this patent is extended or adjusted under 35 U.S.C. 154(b) by 965 days.

(21) Appl. No.: 17/361,883

(22) Filed: Jun. 29, 2021

(65) Prior Publication Data
US 2021/0322012 A1   Oct. 21, 2021

Related U.S. Application Data

(62) Division of application No. 16/363,940, filed on Mar. 25, 2019, now abandoned.
(Continued)

(51) Int. Cl.
*A61B 17/11* (2006.01)
*A61B 17/00* (2006.01)
(Continued)

(52) U.S. Cl.
CPC .......... *A61B 17/1128* (2013.01); *A61L 27/24* (2013.01); *A61L 27/44* (2013.01);
(Continued)

(58) Field of Classification Search
CPC ...... A61B 17/1128; A61B 2017/00526; A61B 2017/00893; A61B 2017/00964; A61B 2017/1132; A61L 27/24; A61L 27/3637; A61L 27/44; A61L 27/48; A61L 27/52; A61L 27/54; A61L 2430/32; B29C 70/68;
(Continued)

(56) References Cited

U.S. PATENT DOCUMENTS 6,214,021 B1 * 4/2001 Hadlock ............ A61B 17/1128
606/152
8,877,498 B2   11/2014 Wegst et al.
(Continued)

FOREIGN PATENT DOCUMENTS

WO      2017015488        1/2017

OTHER PUBLICATIONS

Gan, et al., "Cellulose/soy protein composite-based nerve guidance conduits with designed microstructure for peripheral nerve regeneration", J Neural Eng., Oct. 2016; 13(5).
(Continued)

*Primary Examiner* — Jocelin C Tanner
(74) *Attorney, Agent, or Firm* — Hovey Williams LLP; Crissa A. Cook

(57) ABSTRACT

A composite nerve conduit comprising an elongated body comprising one or more hollow elongated internal channels for guiding and promoting nerve regeneration. The conduit is a three-dimensional scaffold comprising a crosslinked hybrid/composite matrix of collagen and soy protein isolate having improved mechanical and biocompatibility properties. Methods of using the conduit for promoting nerve regeneration at a site of neural tissue damage by bridging wounded, severed, or damaged nerve sections in a peripheral and/or central nervous system. Methods of fabricating composite neural conduits are also disclosed.

12 Claims, 4 Drawing Sheets

Related U.S. Application Data

(60) Provisional application No. 62/648,208, filed on Mar. 26, 2018.

(51) Int. Cl.

| | | |
|---|---|---|
| *A61L 27/24* | (2006.01) | |
| *A61L 27/44* | (2006.01) | |
| *A61L 27/52* | (2006.01) | |
| *B29C 70/68* | (2006.01) | |
| *B29L 31/00* | (2006.01) | |

(52) U.S. Cl.
CPC .............. *A61L 27/52* (2013.01); *B29C 70/68* (2013.01); *A61B 2017/00526* (2013.01); *A61B 2017/00893* (2013.01); *A61B 2017/00964* (2013.01); *A61B 2017/1132* (2013.01); *A61L 2430/32* (2013.01); *B29K 2089/00* (2013.01); *B29L 2031/753* (2013.01)

(58) Field of Classification Search
CPC ........... B29K 2089/00; B29L 2031/753; C08L 89/06
USPC ......................................................... 606/152
See application file for complete search history.

(56) References Cited

U.S. PATENT DOCUMENTS

| | | |
|---|---|---|
| 8,926,886 B2 | 1/2015 | Pandit et al. |
| 2006/0287660 A1* | 12/2006 | Syed ................. A61M 5/14276 606/152 |
| 2011/0276066 A1* | 11/2011 | Pandit ..................... A61L 27/54 427/2.24 |
| 2012/0149111 A1* | 6/2012 | Wegst ................. C12N 5/0619 435/395 |
| 2013/0317582 A1* | 11/2013 | Chen ......................... A61F 7/12 607/116 |
| 2017/0135802 A1* | 5/2017 | McAlpine .............. A61B 34/10 |
| 2017/0224776 A1* | 8/2017 | Chiu ................. A61K 38/1825 |
| 2018/0207232 A1* | 7/2018 | Lelkes ................. A61L 27/222 |

OTHER PUBLICATIONS

Li-Hua, et al., "Physical properties and biocompatibility of cellulose/soy protein isolate membranes coagulated from acetic aqueous solution." Journal Of Biomaterials Science, Polymer Edition, Apr. 2008, 19(4), 479-496.

Luo, et al., "Construction of Nerve Guide Conduits from Cellulose/Soy Protein Composite Membranes Combined with Schwann Cells and Pyrroloquinoline Quinone for the Repair of Peripheral Nerve Defect." Biochemical and Biophysical Research Communications., U.S. National Library of Medicine, Feb. 20, 2015.

Office Action in co-pending U.S. Appl. No. 16/363,940, dated Jan. 4, 2021

* cited by examiner

COMPOSITE NEURAL CONDUIT

CROSS-REFERENCE TO RELATED APPLICATIONS

The present application is a divisional of U.S. patent application Ser. No. 16/363,940, filed Mar. 25, 2019, which claims the priority benefit of U.S. Provisional Patent Application Ser. No. 62/648,208, filed Mar. 26, 2018, entitled COMPOSITE NEURAL CONDUIT, incorporated by reference in its entirety herein.

BACKGROUND

Field of the Invention

The present invention relates to composite neural conduits having improved properties for repair of neural defects and damage.

Description of Related Art

In the field of neural regeneration, neural conduits are used to repair neural defects. Conduits act like a bridge and connect two damaged nerve endings together, providing a channel and scaffold to guide and facilitate nerve growth. As the new nerves grow along the conduit, the two ends can reconnect and restore function. Restoration of function in the peripheral nervous system is possible, but there are a number of factors surrounding the repair of the central nervous system to make it much more challenging.

A variety of conduit designs and compositions have been explored, but success in clinical applications find some materials and configurations are advantageous compared to others. For example, bovine collagen is a common biomaterial that mimics a microenvironment suitable for neural growth, but there are issues with mechanical defects and inflammatory responses occurring.

SUMMARY OF THE INVENTION

The present disclosure is concerned with composite nerve conduits comprising a three-dimensional crosslinked composite matrix of collagen and soy protein isolate configured with one or more hollow elongated internal channels for guiding and promoting nerve regeneration. The neural conduits are fabricated as elongated bodies configured to substantially encircle at least two damaged neural sections in a peripheral and/or central nervous system and bridge any gap therebetween. The matrix material used to form the conduit can consist essentially or even consist of crosslinked collagen and soy protein isolate (including any remaining crosslinker, if applicable).

Methods of promoting nerve regeneration at a site of neural tissue damage by bridging wounded, severed, or damaged nerve sections in a peripheral and/or central nervous system are also described herein. The methods generally comprise one damaged nerve end with a first end of a composite neural conduit according to the various described embodiments, and contacting a second end of the neural conduit with an opposing damaged nerve end, to thus bridge the gap between the damaged sections. In some embodiments, treatment modalities also include applying an electric current to promote regeneration.

The present disclosure also concerns methods of fabricating composite neural conduits according to the various described embodiments. The methods generally comprise providing a biopolymer solution comprising collagen and soy protein isolate dissolved or dispersed in a solvent system. The biopolymer solution is applied to a negative mold to form the body of the conduit. The negative mold is generally configured with one or more elongated removable inserts for forming one or more hollow elongated internal channels within the body. The biopolymer solution is then solidified in the presence of the mold to yield a crosslinked matrix comprising a composite of collagen and soy protein isolate. The crosslinked matrix is then removed from the mold (or vice versa, the mold is removed from the matrix) to yield an elongated body comprising the one or more hollow elongated internal channels extending between respective terminal ends of the body.

The composite/hybrid neural conduits have improved properties over conventional conduit materials, including stronger structural integrity, resiliency, and improved biocompatibility.

DETAILED DESCRIPTION

Figure 1A:
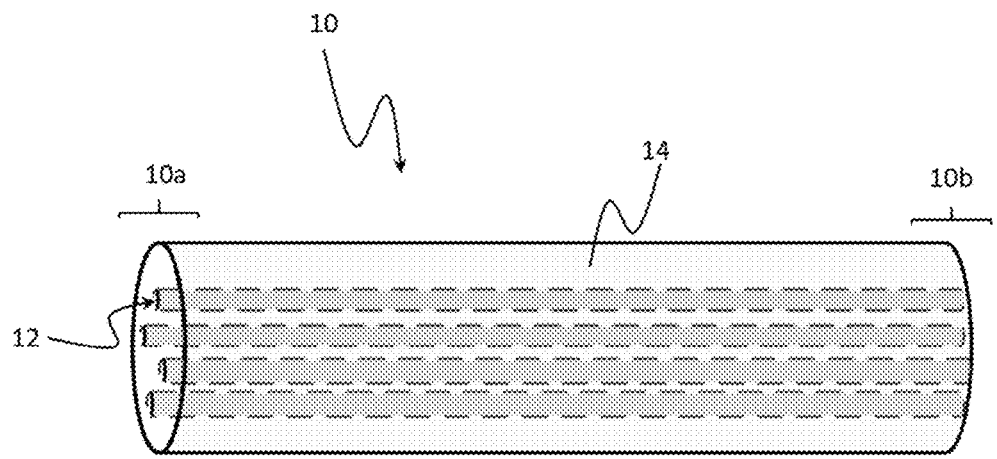
FIG. 1A is a plan view of a composite neural conduit having multiple channels in accordance with an embodiment of the invention.

It is an object of the present invention to provide a neural conduit suitable for the repair of nerves of the peripheral and/or central nervous systems in a patient. Another object of the invention is to provide a biomaterial scaffold with favorable material and mechanical properties. A further object is to provide a multichannel composite nerve conduit with improved physical and biomechanical properties. The composite nerve conduits are biocompatible and biodegradable, and promote the growth of nerves in a regular and controlled manner. Another object is to provide a flexible, but strong nerve conduit material, with decreased inflammatory effects. Composite neural conduits of the invention have greater structural integrity and stiffness as compared to conventional collagen conduits, but retain suitable flexibility and resiliency such that the conduit can flex and bend, but will spring back into its original form after bending. In one or more embodiments, the composite neural conduits have a stiffness (N/mm) of greater than about 6.5, preferably greater than about 7, more preferably greater than about 8. The soy protein isolate in the conduit can be used to modulate the structural and mechanical properties of the fabricated conduits. Further, the composite conduits retain their original form better over time in vivo as compared to conventional collagen conduits, and degrade more slowly than conventional collagen conduits with reduced swelling. Further, the composite neural conduits have improved biocompatibility as compared to conventional collagen conduits, as demonstrated by increased neural outgrowth.

The presented technology is a multi-channel neural conduit with a hybrid composition comprising a mixture of collagen and soy protein isolate as the structural polymer matrix. Soy protein isolate imparts favorable bioactivity, biodegradability, biocompatibility, and processability to the conduit material. Utilizing a hybrid collagen-soy protein isolate conduit results in improved mechanical and biological properties, increasing the ability and likelihood for a nerve defect to be repaired. Advantageously, soy protein isolate reduces immunological and inflammatory responses, while increasing mechanical strength.

The hybrid/composite material comprises an unexpected mixture of animal and plant proteins to promote nerve regeneration, bridging wounded, severed, or damaged nerve sections and allowing the nerve to re-grow along the composite channel(s).

The composite nerve conduit is formed by preparing a biopolymer solution comprising (consisting essentially or consisting of) collagen and soy protein isolate dissolved or dispersed in a solvent system. The biopolymer solution is prepared by mixing collagen and soy protein isolate in a suitable solvent system. For example, separate solutions of collage and soy protein isolate can be first prepared, followed by mixing the solutions in the desired ratios. Alternative, collagen power and/or soy protein isolate powder can be directly mixed into a suitable solvent system. Exemplary solvent systems include glycerol, acetic acid, water, and mixture thereof.

Various weight ratios of collagen and soy protein isolate may be used, depending upon the desired properties of the final matrix. In one or more embodiments, the weight ratio of collagen to soy protein isolate in the biopolymer solution is about from about 20:80 to about 80:20, more preferably from about 30:70 to about 70:30, more preferably from about 40:60 to about 60:40, and even more preferably about 50:50.

Preferably, the collagen is type I collagen, and more preferably collagen extracted from bovine tendon using standard protocols. The collagen is generally provided in powder form before mixing with the solvent system as described. Preferably, the soy protein isolate is 92% SPI (Soy Protein Isolate, MP Biomedicals™). It is appreciated that soy protein isolate contains high levels of genistein, one of the principal isoflavones. In other research, genistein has been shown to act as a kinase inhibitor and has demonstrated immunosuppressive and anti-inflammatory functions. Soy protein isolate provides additional benefits of decreasing the level of proinflammatory cytokine production of mononuclear cells from animal peripheral blood and therefore control immunological reaction. Isoflavones, like genistein, can further improve tissue regeneration and wound healing through an estrogen receptor-independent mechanism. Meanwhile, the soy protein molecule itself has tunable structures and may generate the desirable mechanical properties depending on the processing method. Soy protein isolate may be fabricated into a variety of biomaterial structures including neural conduits and hydrogels. Preferably the soy protein isolate is generally provided in powder form before mixing with the solvent system as described.

The resulting biopolymer solution (comprising or consisting of a mixture of collagen and soy protein isolate) is then molded into the desired geometry for the neural conduit body. Molding may be achieved, for example, by extrusion, injection molding, blow molding, and the like. The viscosity of the biopolymer solution can be adjusted using more or less solvent for the appropriate molding technique. The % by weight of biopolymer in the solution will generally range from about 0.01 to about 20% weight, based upon the total volume of the solution taken as 100%.

In one or more embodiments, the neural conduit body is formed by applying the biopolymer solution around a removable insert that serves as the "negative" for the neural conduit form, such as an elongated wire or tube (e.g., stainless steel wire, plastic, etc.). The negative mold can include a plurality of elongated wires for forming a plurality of internal elongated hollow channels within the neural conduit body when the removable insert is subsequently removed. The biopolymer solution is then solidified around the negative mold.

In one or more embodiments, the biopolymer solution is first air dried to remove residual solvent. In one or more embodiments, the biopolymer solution is then crosslinked. This can be accomplished by addition of one or more crosslinking agents to the biopolymer solution. Exemplary crosslinking agents include 1-ethyl-3-(3-dimethylaminopropyl) carbodiimide (EDC) and N-hydroxysuccinimide (NHS), transglutaminase, glutaraldehyde, sulfonates, genipin, and the like. After crosslinking, the resulting crosslinked matrix should be washed to remove residual crosslinker, e.g., with distilled water and/or monosodium phosphate. After washing, the crosslinked matrix can be lyophilized, followed by removal of the crosslinked matrix from the negative mold. It will be appreciated that alternative crosslinking mechanisms may be used depending upon functionalization of the biopolymers, including thermal crosslinking and photo crosslinking.

Figure 1B:
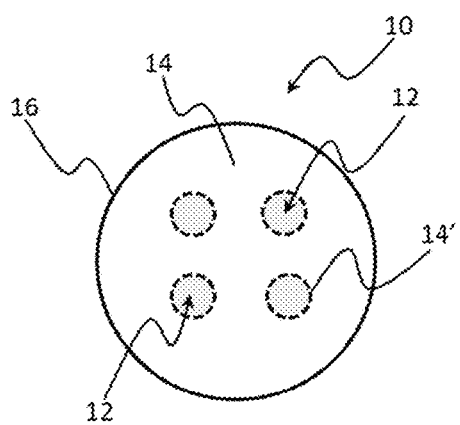
FIG. 1B is a cross-sectional view of the composite neural conduit in FIG. 1A.

The resulting composite neural conduit comprising an elongated body (e.g., single or multi-channel tube) configured for implantation at a site of neural tissue damage for guiding axon regeneration and neural cell migration in order to establish new functional connection across the lesion. The composite neural conduit provides a three-dimensional scaffold for bridging a nerve gap or defect. With reference to FIGS. 1A and 1B, the resulting neural conduit body 10 comprises one or more hollow channels 12 for guiding and promoting nerve regeneration, formed out of the crosslinked composite crosslinked composite matrix 14 of collagen and soy protein isolate and defined by respective interior sidewall surfaces 14'. In general, the body 10 is elongated and extends between two respective terminal ends 10a, 10b so as to fit around or bridge a gap between the two damaged segments of the injured nerve in the patient (not shown). The body 10 presents an external surface 16 and can be cylindrical in shape, such that the radial exterior surface 16 presents a substantially circular axial cross section. However, other geometric shapes are contemplated (e.g., oval, elliptical, polygonal, such as octagonal, etc.) without departing from the teachings of the present invention. The internal channels 12 can likewise be cylindrical with a radial interior sidewall 14' that likewise presents a substantially circular axial cross-section; however, it will be appreciated that the cross-sectional shape will depend upon the shape of the negative form used in molding the channels 12. Thus, it will be readily apparent to one of ordinary skill in the art that the term "radial," as used herein with respect to the conduit, is not limited to substantially circular cross sections and encompasses polygonal cross sections or cross sections presenting other geometric shapes (e.g., oval or elliptical cross sections).

The composite neural conduit matrix that defines the conduit body form is of a resilient, biocompatible material, and the body comprises a first end 10a for connecting to a first end of the damaged nerve, and a second end 10b for connecting to the second end of an opposing damaged nerve. The internal hollow channels 12 of the body 10 extend between the first and second terminal ends 10a, 10b of the conduit body 10 to facilitate rejoining of the damaged nerve ends. The nerve conduit may have a plurality of channels 12, such as 1 or more, preferably 2 or more, more preferably from 2 to 10, more preferably 2 to 7, and even more preferably from 2 to 4 channels. Preferably, the channels are evenly sized and spaced apart. This is achieved by evenly spacing the elongated negative mold forms, and using mold forms of the same size. The neural conduit cross-sectional dimension (e.g., diameter, maximum width, etc.), circumference, length, and channel diameter will vary depending on the species of the patient, size of the nerve, area of injury, and extent of injury to be repaired. A variety of dimensions can be used. Non-limiting examples are described herein. The outer diameter (cross-sectional dimension or width) as measured from the exterior side wall 16 of the nerve conduit body can be up to 4 cm, with the diameter of each channel 12 ranging between about 50 µm and about 4 mm. For a 2-mm diameter conduit, the diameter of respective channels may be about 50 µm to about 700 µm, preferably about 530 µm. It will be appreciated that the channel number and diameter can vary widely, especially depending upon the particular patient. For human patients, the conduit may vary from 1 channel to 100 channels, and the channel diameter can range from about 10 micrometers to 2 cm. In use, the conduit can be cut-to-size, and short lengths of the conduits are generally used, with typical manufactured lengths being 100 mm or less, preferably 75 mm or less, and in some cases 50 mm or less, 30 mm or less, 15 mm or less, 10 mm or less, or 5 mm or less. General dimensions range from 1-2 mm in diameter up to 4-5 mm in diameter, and 5 mm in length up to 100 mm in length for nerves and up to 4 cm in diameter for spinal cord repairs (with lengths ranging from 5 mm to 100 mm).

The term "diameter" is used herein for ease of reference to refer to the largest cross-sectional dimension, aka width, and should not be construed as excluding similarly measured dimensions for conduit geometries that are not circular in their cross-sectional shape. It is further noted that the dimensions of the illustrated body 10 are provided by way of example only and are not to be construed as limiting, as numerous shapes and/or sizes of bodies may be alternatively configured, as will be readily appreciated by one of ordinary skill in the art upon review of this disclosure. Moreover, while the illustrated embodiment includes the plurality of channels 12 being arranged in a configuration of generally equally spaced groupings, such a normal pattern is by way of example only, and is not necessarily required. For instance, the plurality of channels 12 could alternatively be configured in a generally uniform staggered arrangement or an entirely random arrangement, without departing from the teachings of the present invention.

In one or more embodiments, the neural conduit further comprises one or more materials filling the internal hollow channels 12 of the body 10, such as neurotrophic materials, anti-inflammatories, therapeutic agents, antibiotics, or other active agents, for example to support cellular growth and neural regeneration. In one or more embodiments, the neural conduit is filled with hydrogel and/or aligned nanofibers. For purposes of the present disclosure, hydrogel refers to a solid jelly-like material where the liquid component is water. The hydrogel is preferably a network of polymer chains that are hydrophilic, where water is the dispersion medium. The hydrogel is preferably highly absorbent and possess a degree of flexibility very similar to natural neural tissue. The hydrogel preferably comprises at least one component selected from, but not limited to, a collagen/ soy protein composite hydrogel (see Example 3), chitin, chitosan, guar gum, gum karaya, agar, treated agar, fenugreek seed mucilage, soy polysaccharide, gellan gum, mango peel pectin, lepidium sativum mucilage, plantago ovata seed mucilage, aegle marmelos gum (AMG), locust bean gum, ficus indica fruit mucilage, mangifera indica gum (MIG), hibiscus rosa sinesis mucilage and treated agar, dehydrated banana powder (DBP), collagen, fibrin, fibronectin, laminin, hyaluronic acid, polysilozane, polyphosphazene, low-density polyethylene (LDPE), high-density polyethylene (HDPE), plastic, polypropylene (PP), polyvinyl chloride (PVC), polystyrene (PS), nylon, nylon 6, nylon 66, Teflon (polytetrafluoroethylene), thermoplastic polyurethanes (TPU), polylacticoglycolic acid (PLGA), polycaprolactone (PCL), and combinations thereof.

In one aspect, the hydrogel comprises further components in or added to the hydrogel matrix within the channels 12. These further components, include, but are not limited to, neural cells, stem cells, growth factors, proteins, progenitor cells, therapeutic peptides, gene vectors, siRNA, miRNA, chemical compounds, and combinations thereof. In one or more embodiments, the composite neural conduit is essentially free of any other additives or components, except those expressly described herein, such as coatings, metals, support structures, and the like. The term "essentially free" means that such component is not intentionally added (although residual amounts or impurities of the component may be present).

Also contemplated herein are methods of promoting nerve regeneration in peripheral and/or central nervous systems, using the composite neural conduits. The methods comprise connecting a first end of a composite neural conduit according to the invention with one end, either rostral or caudal stump, of the damaged spinal cord or nerve. The second end of the composite neural conduit is connected with an opposing damaged nerve end. The neural conduit can be secured in place using any suitable biocompatible technique, including suturing. Such attachment means may be a perforation down the length of the neural conduit so that it may be wrapped around the area where the neural cell or nervous tissue has been injured, and sutured into place if desired. Thus, in the method, the composite neural conduit is generally implanted at a "site of nerve tissue damage," which refers to the damaged segment itself, as well as (relatively) undamaged adjacent segments or stumps on either side of the damaged segment (or gap). The type of nerve injury may be any damage to neural cells or nervous tissue within the body of the patient. The damaged segment may be compression, lesion, tear, or the like, or may include a completely transected nerve. The nerve injury can occur in central nervous system (CNS) or the peripheral nervous system (PNS). Injuries of the CNS may occur anywhere in the CNS, such as, but not limited to the spinal cord or brain. Injuries of the PNS may occur anywhere in the PNS, such as body extremities, but not limited to, face, arms, hands, legs, feet, or phalanges. In a preferred embodiment, the nerve injury is preferably selected from, but not limited to spinal cord injury, nerve injury, neuropraxia, axonotmesis, and neurotmesis.

Additional methods of promoting nerve regeneration may include the application of electrical stimulation to a damaged nerve bridged by the composite neural conduit. The application of electrical stimulation to a damaged nerve segment may act as a therapeutic regimen for promoting unidirectional cell migration and axonal growth through a neural conduit. In one or more embodiments, electrical stimulation may be delivered to the damaged nerve site by an electrode comprising an anodal electrode and cathodal electrode. In one or more embodiments, the anodal electrode may be applied to a rostral stump of damaged nerve (i.e., upstream of the injured or damaged portion). In one or more embodiments, the cathodal electrode may be applied to a composite neural conduit that is bridging the defect, injury, or lesion in the damaged nerve. Exemplary approaches for electrical stimulation are described in Int'l Pub. No. WO/2018/232145 (PCT/US2018/037585), filed Jun. 14, 2018, incorporated by reference herein in its entirety.

The patient for purposes of this disclosure may be any human or animal having a neural injury. Non-limiting examples include, human and non-human mammals, such as dogs, cats, equine, bovine, or porcine subjects, goats, rodents (e.g., rats, rabbits, mice), elephants, monkeys, gorillas, zebras, camels, lions, tigers, bears, and the like.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

The present invention is susceptible of embodiment in many different forms. While the drawings illustrate, and the specification describes, certain preferred embodiments of the invention, it is to be understood that such disclosure is by way of example only. There is no intent to limit the principles of the present invention to the particular disclosed embodiments.

EXAMPLES

The following examples set forth methods in accordance with the invention. It is to be understood, however, that these examples are provided by way of illustration and nothing therein should be taken as a limitation upon the overall scope of the invention.

Example 1—General Protocol

Fabrication of Multichannel Collagen-Soybean Neural Conduits

Soybean protein isolate (SPI) solutions will be prepared by slowly dissolving the SPI with constant stirring in distilled water with the concentration of 3-15% w/v. The pH may be adjusted to 7.2 with 1M sodium hydroxide or 1M HCl. Then glycerol, 50% w/w, (relative to SPI) will be added to the solution with constant stirring, which helps to stabilize the SPI in solution. The solution will be heated at a constant temperature of 55° C. for 30 min and cooled at room temperature. Then the soybean solution will be mixed with type I collagen solution (10 mg/ml, in acetic acid) as different SPI to collagen ratios (weight to weight) to fabricate neural conduits. The neural conduits are fabricated using the type I collagen-SPI composite according to fabrication methods described in U.S. Pat. No. 8,926,886, incorporated by reference in its entirety herein. Briefly, collagen-SPI solution sequentially self-assembles on the molds with insertion of stainless-steel wires. Then the conduit will be crosslinked with EDC and NHS. After washing with $NaH_2PO_4$ (0.1 M) and distilled water, the composite is freeze-dried on the wires. Molds and wires will be removed from the neural conduits after freeze-drying.

Example 2—Composite Neural Conduit

Figure 2:
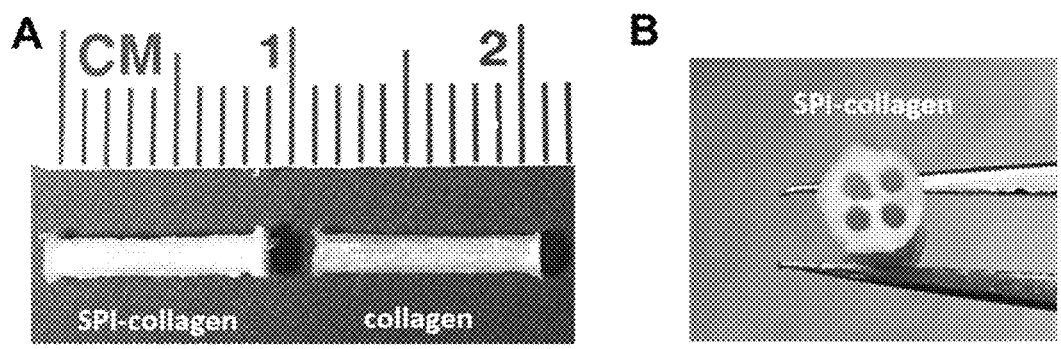
FIG. 2 shows a photographic image of the SPI-collagen composite 4-channel conduit fabricated in Example 2 and compared with a traditional collagen conduit (left panel), and a photographic image of a cross-section of the SPI-collagen composite 4-channel conduit (right panel)

1. Fabrication and Mechanical Properties 1.1 Fabrication of Multichannel Collagen-Soybean Neural Conduits Soybean protein isolate (SPI) solutions were prepared by slowly dissolving the SPI (Soy Protein Isolate, MP Biomedicals™) with constant stirring in distilled water with the concentration of 10% w/v. Then glycerol, 50% w/w, (relative to SPI) was added to the solution with constant stirring. The solution was heated at a constant temperature of 55° C. for 30 min and cooled at room temperature. Then the soybean solution was mixed with type I collagen solution (isolated in lab from bovine tendon; 10 mg/ml, in 50 mM acetic acid) as 1:1 protein weight ratio to fabricate neural conduits. Then 4-channel conduits were fabricated. The matrix was crosslinked with 30 m EDC and 20 mM NHS. After washing with $NaH_2PO_4$ (0.1 M) and distilled water, the collagen was freeze-dried on the wires. The resulting conduits are shown in FIG. 2.

1.2 Mechanical Property of the Neural Conduits

Figure 3:
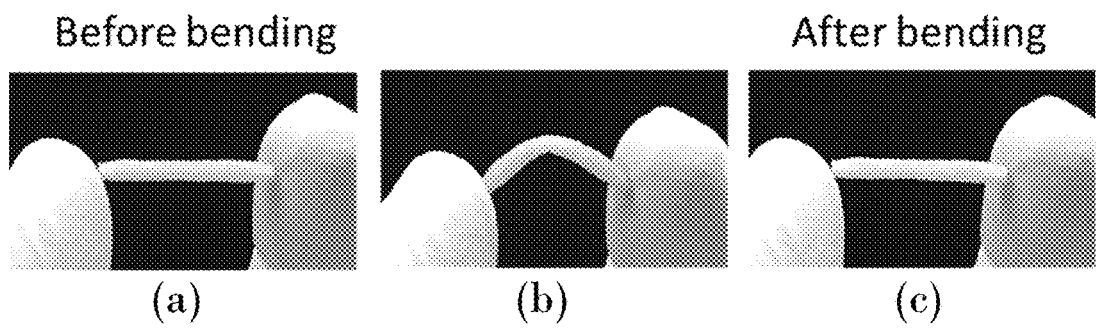
FIG. 3 is a photographic image of the bending test to show the flexibility and resiliency of the SPI-collagen composite 4-channel conduit (a) before, (b) during, and (c) after manually bending a length of the conduit tube in half.
Figure 4:
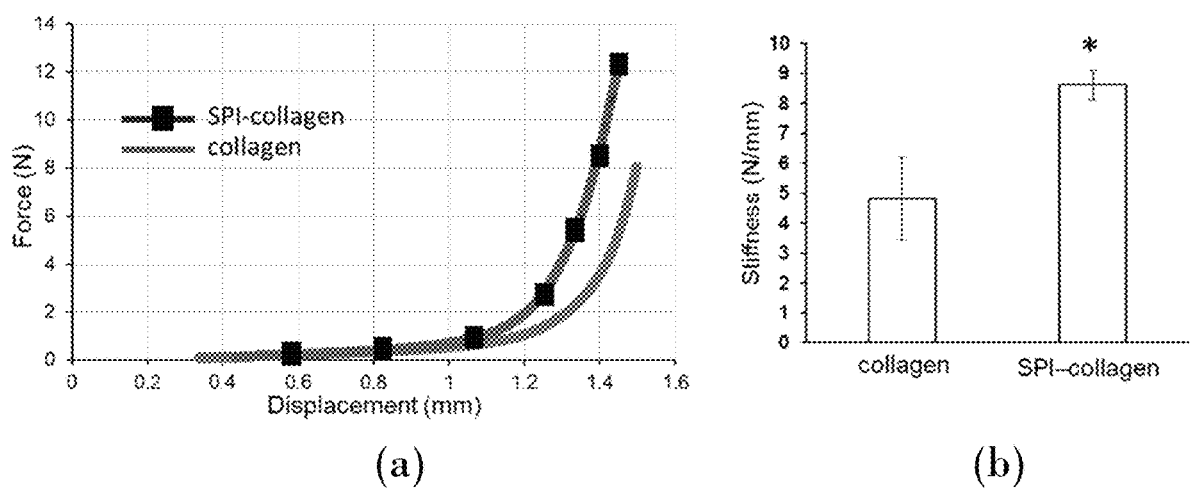
FIG. 4 is a graph showing the data from the compressive test of neural conduits showing the (a) flexibility/resiliency; and (b) stiffness of the conduits.

Mechanical properties of multichannel conduits were characterized by compressive tests. The compressive tests were performed on the fabricated neural conduits using a uniaxial test machine (ELF 3200 Endura-Tec, Schaumburg, Ill.). FIGS. 3 and 4 show that the stiffness of SPI-collagen is higher than the collagen conduits, and its resiliency is improved.

2. Chemical Properties

2.1 Fourier Transform Infrared Spectroscopy (FTIR) Assay

Figure 5:
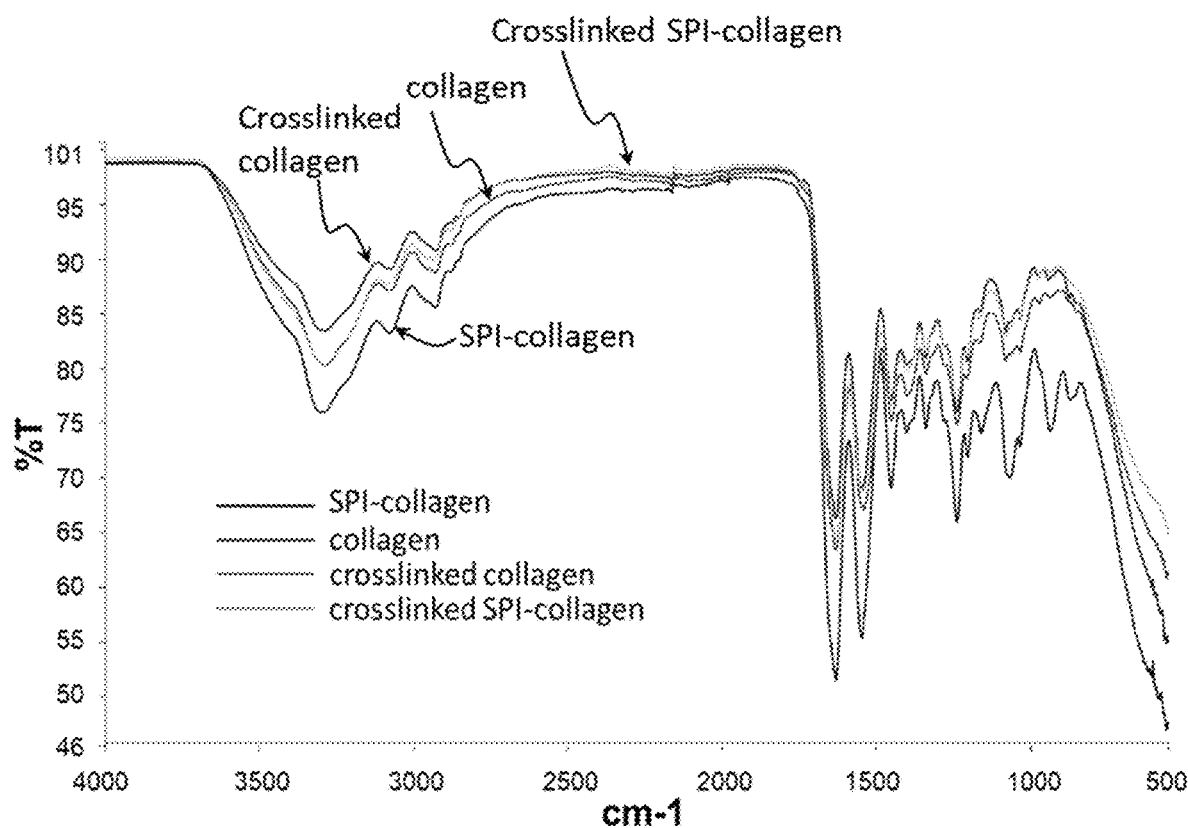
FIG. 5 is a graph showing the data from the FTIR test comparing SPI-collagen composite and collagen conduits.

Fourier transform infrared spectroscopy (FTIR) was performed to study the chemical bond formation of collagen-SPI hydrogels with or without crosslinking. Spectra was obtained using a Spectrum 100 FT-IR Spectrometer Perkin Elmer (PerkinElmer). FIG. 5 confirms the crosslinking of the conduits by EDC/NHS.

2.2 Degradation Test

Figure 6:
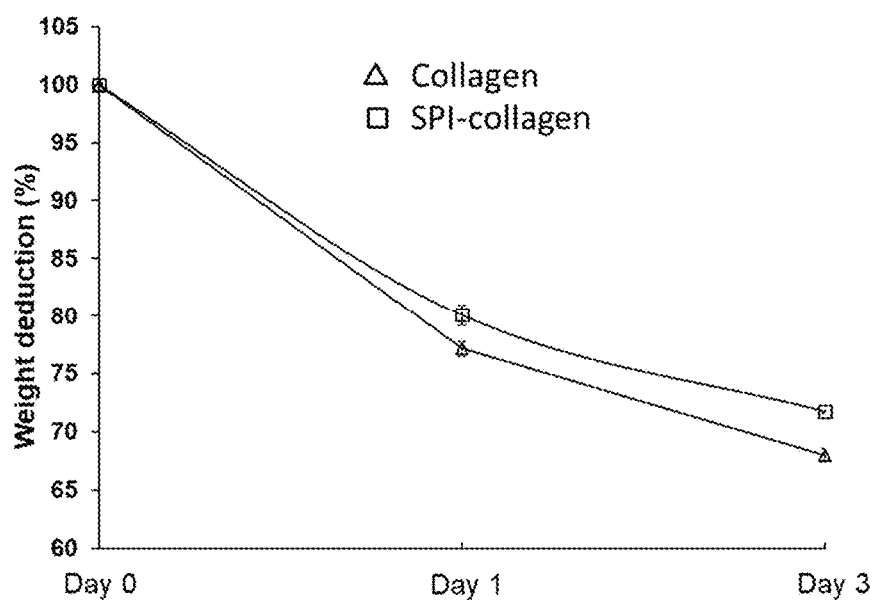
FIG. 6 is a graph of the data for the degradation study of SPI-collagen composite conduits and collagen conduits.

Bacterial collagenase was used to study the degradation profile of collagen conduits. The enzyme was dissolved in a 0.1 M Tris-HCl buffer (pH 7.4) solution containing 0.005 M $CaCl_2$. After 1-day and 3-day incubation of the samples with the enzyme solution, the remaining pellet were repeatedly washed with distilled water and then freeze-dried. The samples were then be weighed. FIG. 6 shows that SPI-collagen conduits and collagen conduits are biodegradable by collagenase.

2.3 Conduit Swelling Test

Figure 7:
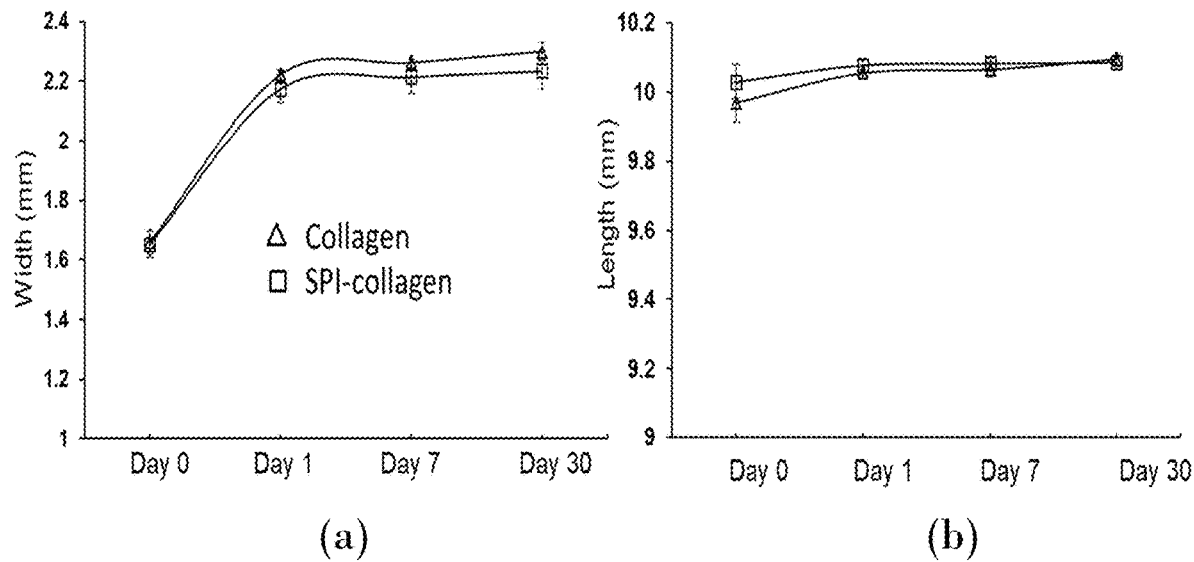
FIG. 7 is a graph of the data for the swelling test of the conduits, showing changes in (a) width and (b) length of a given fabricated conduit.

The neural conduits were placed in PBS (pH 7.4). The length and width of the conduits were studied at time points of immediately before incubation and at day 1, 7 and 30 after incubation. The length and width of conduits were measured with a digital caliper. The results are shown in FIG. 7, panels (a) and (b).

3. Biocompatibility

Figure 8:
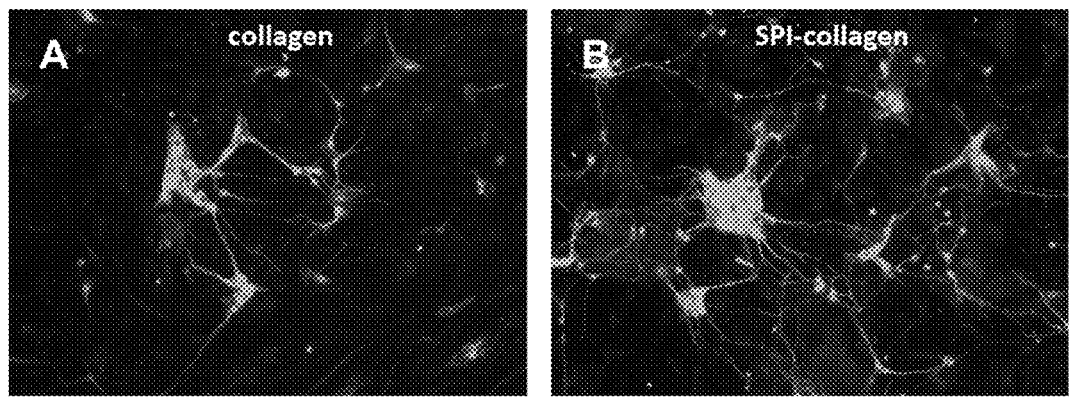
FIG. 8 shows images of neural cell growth on A) collagen and B) SPI-collagen composite, in which the cells are labeled with anti-βIII tubulin antibody.

3.1 The Study of Neurite Outgrowth from Human-Induced Pluripotent Stem Cell-Derived Neurons on Collagen-Soybean Composite Films Collagen films were fabricated by spreading the collagen-SPI solution on a flat Teflon surface (weigh boat) and air-dried. The collagen films were then crosslinked with EDC and NHS as above. The induced pluripotent stem cell-derived neurons were grown on the films. The study showed the extensive neurite growth on SPI-collagen films. The study indicates that the crosslinked SPI-collagen films are biocompatible, and have improved biocompatibility as compared to collagen, as shown in the images in FIG. 8.

Example 3—Composite Neural Hydrogel

1. Fabrication and Mechanical Properties

1.1 Fabrication of a Composite Collagen-Soybean Hydrogels

SPI solutions are prepared by adding SPI powder in distilled water with the concentration of 1-10% w/v. Then, glycerol is added to the SPI solution under mechanical stirring at a constant temperature of 55° C. for 30 min and cooled at room temperature.

The SPI solution is mixed with type I collagen solution (in acetic acid) at various weight ratios, respectively, to form an SPI/collagen solution. To form the hydrogel, the pH value of the SPI/collagen solution is adjusted to 7 by adding a NaOH aqueous solution (1M) and phosphate-buffered saline (PBS) solution (10×). The gelation takes place by incubating the SPI/collagen solution in the 37° C. incubator.

The mixture of SPI-collagen solution is crosslinked with 4S-StarPEG at various concentrations. The final 4S-Star-PEG concentrations in the SPI-collagen will range between 0.05 mM and 8 mM. A collagen hydrogel lacking crosslinker will be used as a control.

The invention claimed is:

1. A method of promoting nerve regeneration at a site of neural tissue damage by bridging wounded, severed, or damaged nerve sections in a peripheral and/or central nervous system, said method comprising:
   contacting one damaged nerve end with a first end of a composite neural conduit, and
   contacting a second end of the neural conduit with an opposing damaged nerve end,
   wherein the composite neural conduit comprises a flexible and resilient elongated body comprising one or more hollow elongated internal channels for guiding and promoting nerve regeneration, each of said one or more hollow elongated internal channels defined by a sidewall comprising a crosslinked composite matrix of collagen and soy protein isolate, said elongated body having respective first and second terminal ends, wherein each of said one or more hollow elongated internal channels extends between the first and second ends of the elongated body.

2. The method of claim 1, said composite neural conduit comprising two or more of said hollow elongated internal channels for guiding and promoting nerve regeneration.

3. The method of claim 1, said elongated body of the composite neural conduit having a cross-sectional dimension of from about 1 mm to about 4 cm and a length of from about 5 mm to about 100 mm.

4. The method of claim 1, wherein the composite neural conduit is configured to substantially encircle said damaged nerve ends and bridge any gap therebetween.

5. The method of claim 1, wherein the composite neural conduit comprises one or more additional elements selected from the group consisting of growth factors, stem cells, neural cells, progenitor cells, gene vectors, proteins, therapeutic peptides, siRNA, miRNA, chemical compounds, and combinations thereof adsorbed thereon or therein.

6. The method of claim 1, wherein said one or more hollow elongated internal channels is filled with a hydrogel comprising at least one material selected from the group consisting of a collagen/soy protein composite, chitin, chitosan, guar gum, gum karaya, agar, treated agar, fenugreek seed mucilage, soy polysaccharide, gellan gum, mango peel pectin, lepidium sativum mucilage, plantago ovata seed mucilage, aegle marmelos gum, locust bean gum, ficus indica fruit mucilage, mangifera indica gum, hibiscus rosa sinesis mucilage and treated agar, dehydrated banana powder, collagen, fibrin, fibronectin, laminin, hyaluronic acid, polysilozane, polyphosphazene, low-density polyethylene, high-density polyethylene, plastic, polypropylene, polyvinyl chloride, polystyrene, nylon, nylon-6, nylon-66, polytetrafluoroethylene, thermoplastic polyurethanes, polylactico-glycolic acid, polycaprolactone, and combinations thereof.

7. The method of claim 1, wherein said composite neural conduit sidewall consists essentially of said crosslinked composite matrix of collagen and soy protein isolate.

8. The method claim 1, wherein said soy protein isolate is 92% soy protein isolate and comprises genistein.

9. The method of claim 1, wherein said composite neural conduit comprises a weight ratio of collagen and soy protein isolate of from about 20:80 to about 80:20.

10. The method of claim 1, wherein said collagen is type I collagen.

11. The method of claim 1, further comprising applying an electric current to said site of neural tissue damage.

12. The method of claim 11, wherein said electric current is configured to generate a unidirectional electric field at said site of nerve tissue damage from one damaged nerve end to the opposing damaged nerve end.

* * * * *